United States Patent
Ellenbogen et al.

(10) Patent No.: US 11,927,755 B2
(45) Date of Patent: Mar. 12, 2024

(54) SEE-THROUGH DISPLAY FOR AN AUGMENTED REALITY SYSTEM

(71) Applicant: Technology Innovation Momentum Fund (Israel) Limited Partnership, Tel-Aviv (IL)

(72) Inventors: Tal Ellenbogen, Tel-Aviv (IL); Ori Avayu, Tel Aviv (IL); Ran Ditcovski, Tel-Aviv (IL)

(73) Assignee: Technology Innovation Momentum Fund (Israel) Limited Partnership, Tel-Aviv (IL)

( * ) Notice: Subject to any disclaimer, the term of this patent is extended or adjusted under 35 U.S.C. 154(b) by 462 days.

(21) Appl. No.: 17/268,468

(22) PCT Filed: Sep. 27, 2018

(86) PCT No.: PCT/IB2018/057504
§ 371 (c)(1),
(2) Date: Feb. 14, 2021

(87) PCT Pub. No.: WO2020/065380
PCT Pub. Date: Apr. 2, 2020

(65) Prior Publication Data
US 2021/0181515 A1 Jun. 17, 2021

(51) Int. Cl.
*G02B 27/01* (2006.01)
*F21V 8/00* (2006.01)
(Continued)

(52) U.S. Cl.
CPC ......... *G02B 27/0172* (2013.01); *G02B 1/002* (2013.01); *G02B 6/005* (2013.01);
(Continued)

(58) Field of Classification Search
CPC ................ G02B 27/0172; G02B 6/005; G02B 2027/0118; G02B 2027/0138;
(Continued)

(56) References Cited

U.S. PATENT DOCUMENTS

| 3,992,574 A | 11/1976 | Bouwhuis et al. |
| 10,310,287 B2 | 6/2019 | Ellenbogen |

(Continued)

FOREIGN PATENT DOCUMENTS

| EP | 1128197 | 8/2001 |
| JP | 2006-350232 | 12/2006 |

(Continued)

OTHER PUBLICATIONS

Official Action dated Dec. 13, 2021 from US Patent and Trademark Office Re. U.S. Appl. No. 16/482,717. (38 pages).

(Continued)

*Primary Examiner* — Tina M Wong

(57) ABSTRACT

An optical system for a see-through display includes a stack of metasurface layers configured to receive light constituting an image; and a waveguide coupled to the stack. Each layer in the stack of metasurface layers is configured to provide a resonant response to an optical field at a different spectral band and to couple the resonant response with a waveguide. The waveguide is configured to propagate the different spectral bands in a direction of a user's eye.

27 Claims, 11 Drawing Sheets
(6 of 11 Drawing Sheet(s) Filed in Color)

(51) Int. Cl.
*G02B 1/00* (2006.01)
*G06F 3/01* (2006.01)
*H04N 23/54* (2023.01)
*H04N 23/56* (2023.01)

(52) U.S. Cl.
CPC ......... *G02B 27/0179* (2013.01); *G06F 3/013* (2013.01); *H04N 23/54* (2023.01); *H04N 23/56* (2023.01); *G02B 2027/0118* (2013.01); *G02B 2027/0138* (2013.01); *G02B 2027/014* (2013.01); *G02B 2027/0187* (2013.01)

(58) Field of Classification Search
CPC ...... G02B 2027/014; G02B 2027/0187; G02B 1/002; H04N 25/54; H04N 25/56
See application file for complete search history.

(56) References Cited

U.S. PATENT DOCUMENTS

| | | | |
|---|---|---|---|
| 10,485,445 | B2 | 11/2019 | Palikaras |
| 11,137,617 | B2 | 10/2021 | Ellenbogen et al. |
| 2005/0073744 | A1 | 4/2005 | Zheludev et al. |
| 2007/0014006 | A1 | 1/2007 | Tanaka et al. |
| 2008/0088524 | A1 | 4/2008 | Wang et al. |
| 2008/0089645 | A1 | 4/2008 | Wang et al. |
| 2008/0198453 | A1 | 8/2008 | LaFontaine et al. |
| 2009/0296236 | A1 | 12/2009 | Bowers et al. |
| 2010/0053608 | A1 | 3/2010 | Lee |
| 2010/0054105 | A1 | 3/2010 | Handa |
| 2010/0141358 | A1 | 6/2010 | Akyurtlu et al. |
| 2010/0142014 | A1 | 6/2010 | Rosen et al. |
| 2012/0113502 | A1 | 5/2012 | Suh et al. |
| 2012/0267549 | A1 | 10/2012 | Crozier et al. |
| 2013/0077049 | A1 | 3/2013 | Bohn |
| 2013/0208332 | A1 | 8/2013 | Yu et al. |
| 2013/0342898 | A1 | 12/2013 | Alvine et al. |
| 2015/0380829 | A1 | 12/2015 | Lee-Bouhours et al. |
| 2016/0259175 | A1 | 9/2016 | Ellenbogen et al. |
| 2016/0306079 | A1 | 10/2016 | Arbabi et al. |
| 2016/0353039 | A1 | 12/2016 | Rephaeli et al. |
| 2017/0003169 | A1 | 1/2017 | Shaltout et al. |
| 2017/0131460 | A1 | 5/2017 | Lin et al. |
| 2017/0293141 | A1 | 10/2017 | Schowengerdt et al. |
| 2017/0310907 | A1 | 10/2017 | Wang |
| 2018/0217395 | A1 | 8/2018 | Lin et al. |
| 2018/0252857 | A1 | 9/2018 | Glik et al. |
| 2019/0265498 | A1 | 8/2019 | Ellenbogen et al. |
| 2020/0284960 | A1 | 9/2020 | Ellenbogen et al. |
| 2022/0026731 | A1 | 1/2022 | Ellenbogen et al. |

FOREIGN PATENT DOCUMENTS

| | | |
|---|---|---|
| WO | WO 2005/057247 | 6/2005 |
| WO | WO 2011/139785 | 11/2011 |
| WO | WO 2013/033591 | 3/2013 |
| WO | WO 2013/033591 | 5/2013 |
| WO | WO 2015/063762 | 5/2015 |
| WO | WO 2018/142339 | 8/2018 |
| WO | WO 2020/065380 | 4/2020 |

OTHER PUBLICATIONS

Communication Pursuant to Rule 164(1) EPC [Supplementary Partial European Search Report and the Provisional Opinion] dated Jun. 30, 2017 From the European Patent Office Re. Application No. 14857816.4. (12 Pages).
Corrected Supplementary European Search Report and the European Search Opinion dated Jan. 16, 2018 From the European Patent Office Re. Application No. 14857816.4. (12 Pages).
International Preliminary Report on Patentability dated May 12, 2016 From the International Bureau of WIPO Re. Application No. PCT/IL2014/050932.
International Preliminary Report on Patentability dated Aug. 15, 2019 From the International Bureau of WIPO Re. Application No. PCT/IB2018/050668. (7 Pages).
International Search Report and the Written Opinion dated May 3, 2018 From the International Searching Authority Re. Application No. PCT/IB2018/050668. (11 Pages).
International Search Report and the Written Opinion dated Feb. 17, 2015 From the International Searching Authority Re. Application No. PCT/IL2014/050932.
International Search Report and the Written Opinion dated Jan. 24, 2019 From the International Searching Authority Re. Application No. PCT/IB2018/057504. (14 Pages).
Official Action dated Mar. 9, 2021 From the US Patent and Trademark Office Re. U.S. Appl. No. 16/406,045. (17 Pages).
Official Action dated May 14, 2018 From the US Patent and Trademark Office Re. U.S. Appl. No. 15/032,418. (19 pages).
Supplementary European Search Report and the European Search Opinion dated Sep. 11, 2017 From the European Patent Office Re. Application No. 14857816.4. (16 Pages).
Aieta et al. "Aberration-Free Ultrathin Flat Lenses and Axicons at Telecom Wavelengths Based on Plasmonic Metasurfaces", Nano Letters, 12: 4932-4936, Aug. 15, 2012.
Avayu et al. "Ultrathin Full Color Visor With Large Field of View Based on Multilayered Metasurface Design", Digital Optics for Immersive Displays, Proceedings of the SPIE, 1067612: 1067612-1-1067612-7, May 21, 2018.
Chen et al. "Dual-Polarity Plasmonic Metalens for Visible Light", Nature Communications, 3: 1198-1-1198-6, Nov. 13, 2012.
Ellenbogen et al. "Nonlinear Generation and Manipulation of Airy Beams", Nature Photonics, 3: 395-398, Jul. 2009.
Fu et al. "Experimental Investigation of Superfocusing of Plasmonic Lens With Chirped Circular Nanoslits", Optics Express, 18(4): 3438-3443, Feb. 15, 2010.
Giannini et al. "Plasmonic Nanoantennas: Fundamentals and Their Use in Controlling the Radiative Properties of Nanoemitters", Chemical Reviews, 111(6): 3888-3912, Mar. 24, 2011.
Lin et al. "Polarization-Controlled Tunable Directional Coupling of Surface Plasmon Polaritons", Science 340: 331-334, Apr. 19, 2013.
Liu et al. "Three-Dimensional Photonic Metamaterials at Optical Frequencies", Nature Materials, 7(1): 31-37, Published Online Dec. 2, 2007.
Siviloglou et al. "Accelerating Finite Energy Airy Beams", Optics Letters, 32(8): 979-981, Apr. 15, 2007.
Wan et al. "Control the Dispersive Properties of Compound Plasmonic Lenses", Optics Communicationa, XP055384689, 291: 390-394, Available Online Dec. 5, 2012. Section 3, Figs.1-4.
Young "Zone Plates and Their Aberrations", Journal of the Optical Society of America, 62(8): 972-976, Aug. 1972.
Zhao et al. "A Reconfigurable Plasmofluidic Lens", Nature Communications, 4(2305): 1-8, Aug. 9, 2013.
Official Action dated Jun. 8, 2023 from the US Patent and Trademark Office Re. U.S. Appl. No. 17/492,765. (22 pages).
Official Action dated Aug. 12, 2022 from US Patent and Trademark Office Re. U.S. Appl. No. 16/482,717. (31 pages).
Notice of Allowance dated Sep. 20, 2023 from the US Patent and Trademark Office Re. U.S. Appl. No. 17/492,765. (12 pages).
Grounds of Reason of Rejection dated Jul. 17, 2023 From the Korean Intellectual Property Office Re. Application No. 10-2021-7011443 and Its Translation Into English. (15 Pages).
Notice of Allowance dated Aug. 2, 2023 from the US Patent and Trademark Office Re. U.S. Appl. No. 16/482,717. (13 pages).

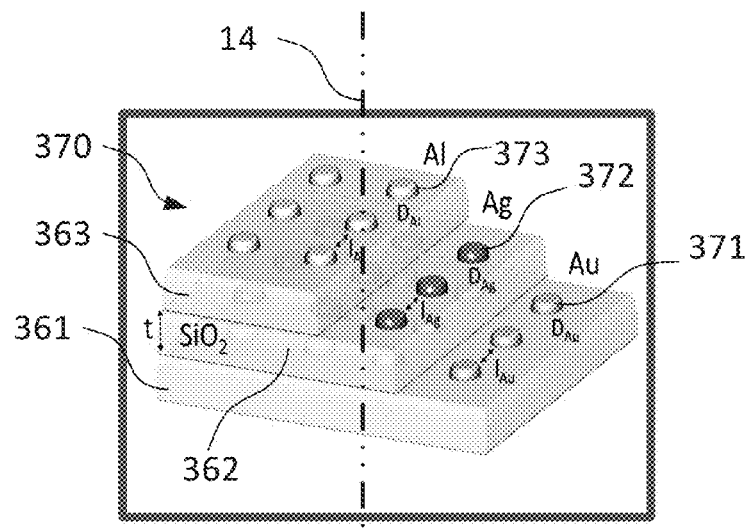
FIG. 5
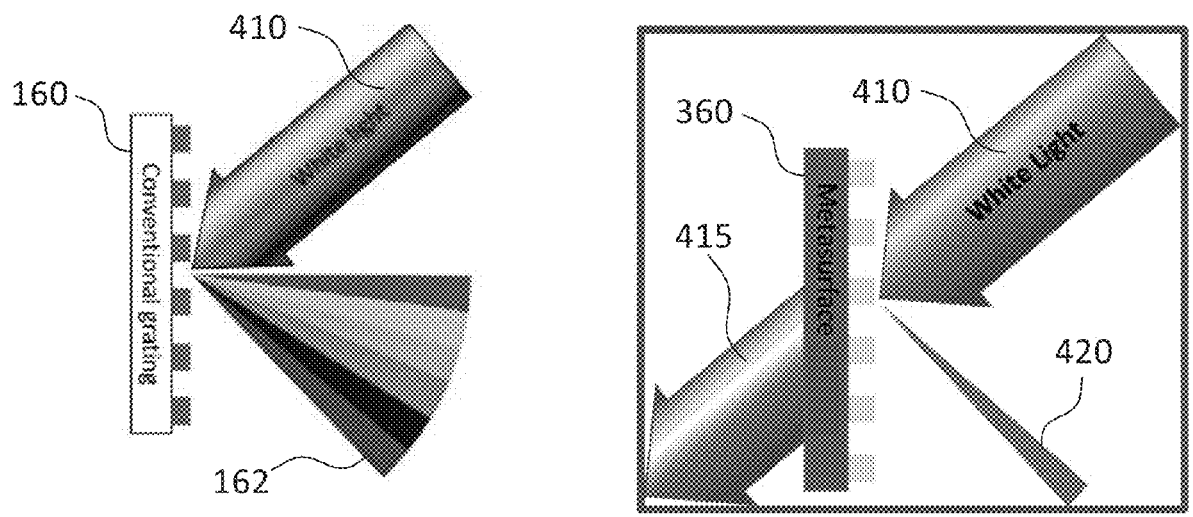
FIG. 6A
FIG. 6B

SEE-THROUGH DISPLAY FOR AN AUGMENTED REALITY SYSTEM

RELATED APPLICATION(S)

This application is a National Phase of PCT Patent Application No. PCT/IB2018/057504 having International filing date of Sep. 27, 2018, the contents of which are all incorporated by reference as if fully set forth herein in their entirety.

FIELD AND BACKGROUND OF THE INVENTION

The present invention, in some embodiments thereof, relates to a see-through display and, more particularly, but not exclusively, to a near-eye visor. In preferred embodiments, the near-eye visor serves as a display of an augmented reality system.

Near-eye visors for augmented reality systems are typically transparent to visible light. Form factor of near-eye visors is a parameter in promoting widespread acceptance of augmented reality systems at least for consumer electronics applications. Attempts have been made to replace some bulk optics, e.g. free-form optics, with more compact and light-weight elements. Example elements include diffractive optical elements (DOEs) or holographic optical elements (HOEs) designed to couple light in and out of a waveguide (WG) in transmission or reflection mode. The chromatic aberrations of DOEs and (HOEs) however, are large, and therefore not suited for a broadband spectrum of visual light. One solution is to use several layers of WGs with each WG layer supporting a different wavelength.

Another parameter is the angular field-of-view (FOV), defined as the angle of acceptance of light rays by the user's eye. Known systems feature a FOV of less than half of the human FOV, and therefore fail to provide the user with an immersive experience.

Optical metasurfaces (MSs) are artificially engineered surfaces at the nanometer scale, which allow the control of optical response. MSs are composed of a dense array of either dielectric or metallic building blocks, and the optical properties of the MS are usually governed by the single building block response. These surfaces are ultra-thin (tens of nanometers), relatively easy to fabricate, and allow optical control.

International Patent Publication No. WO2018/142339, entitled "Multilayer Optical Element For Controlling Light," the contents of which is incorporated herein by reference, describes a multilayer optical element including a plurality of layers arranged along an optical axis, each layer having a plurality of nano-structures, wherein a size of, and a spacing between the nano-structures is selected to provide a resonant response to an optical field at different wavelengths for different layers.

SUMMARY OF THE INVENTION

According to an aspect of some embodiments, there is provided a display that is see-through, has a favorable form factor and improved chromatic behavior. A see-through display as defined herein is a display that is at least partially transparent to light in the visible range to visible light. In some example embodiments, the see-through display is a near-eye visor for an augmented reality system. According to some example embodiments, the see-through display includes a visibly transparent stack of MS layers configured to couple a relatively broadband signal in and out of a single waveguide (WG). The ability to use a single WG provides for reducing width of the display. Each layer in the MS stack may act as provide a resonant response at a defined spectral band and may be designed to couple a relatively narrow band surrounding a center wavelength of choice, while substantially keeping the rest of the relevant spectrum unaffected. A relatively broadband for the visual spectrum may be a bandwidth that is at least 150-200 nm wide. A relatively narrow bandwidth may be a bandwidth that is less than 150 nm wide. The MS stack may overcome the dispersive nature of conventional diffractive gratings and may provide for coupling broadband signals to a single WG with a substantially spectrally-uniform field of view (FOV). In some example embodiments, the stack of MS layers is configured to couple a full color image from a virtual image projector, e.g., a display or a micro-display into a user's eye with reduced chromatic aberrations.

As used herein, full color image is defined as an image that spans at least over the range of 400-700 nm.

According to some example embodiments, the see-through display is also configured for directing radiation from a user's eye to a camera, for example, for tracking eye gaze. Optionally, radiation in the non-visible spectrum is applied for this purpose. For example, the radiation can be in the infrared (IR) range, or the near infrared (NIR) range. In some example embodiments, an IR-transparent or NIR-transparent MS layer is configured to direct light projected from an IR or NIR light source toward a user's eye via a WG and direct light reflected from the eye to an eye gazing detector via the WG. Such an MS layer may be part of the stack of MS layers that are otherwise operating in the visible spectrum or may be a separate layer integrated in the see-through display.

According to an aspect of some embodiments, there is also provided an MS layer that is configured to increase coupling efficiency at which the MS layer couples light into or out of the WG, e.g. light in the visible or non visible spectrum. In some example embodiments, the design includes on one or more of uniquely shaped nano-structures forming the layer and a unique defined spatial pattern of the nano-structures in the layer.

According to an aspect of some example embodiments, there is provided an optical system for a see-through display, the system comprising: a stack of metasurface (MS) layers configured to receive light constituting an image; and a waveguide (WG) coupled to said stack, wherein each layer in the stack of MS layers is configured to provide a resonant response to an optical field at a different spectral band and to couple the resonant response with a WG, wherein the WG is configured to propagate the different spectral bands in a direction of a user's eye.

Optionally, the stack of MS layers includes a first layer configured to initiate a resonant response to red light, a second layer configured to initiate a resonant response to green light and a third layer configured to initiate a resonant response to blue light.

Optionally, the stack of MS layers is an input coupler configured to couple light from the external source to the WG.

Optionally, the stack of MS layers is an output coupler configured to couple light in the WG to the user's eye.

Optionally, the stack of MS layers is a first stack of MS layers configured to couple light from the external source to the WG and further comprising a second stack of MS layers configured to couple light in the WG to the user's eye.

Optionally, the first stack of MS layers and the second stack of MS layers are configured to span a same spectral band.

Optionally, each layer in the stack of MS layers is configured as a binary diffractive element.

Optionally, the WG provides total internal reflection (TIR) therein.

Optionally, each layer in the stack of MS layers comprises nano-structures made of a different material.

Optionally, the different material is different metal or dielectric material.

Optionally, the stack of MS layers comprises a layer having gold nano-structures sized and spaced apart to provide a resonant response to an optical field at a first wavelength.

Optionally, the stack of MS layers comprises a layer having silver nano-structures sized and spaced apart to provide a resonant response to an optical field at a second wavelength being shorter than the first wavelength.

Optionally, the stack of MS layers comprises a layer having aluminum nano-structures sized and spaced apart to provide a resonant response to an optical field at a third wavelength being shorter than the second wavelength.

Optionally, the stack of MS layers is configured to be a directional coupler.

Optionally, the nano-structures of at least one layer of the stack of MS layers are configured to have an asymmetrical shape.

Optionally, the nano-structures of at least one layer of the stack of MS layers distributed in a Yagi-Uda antenna configuration.

Optionally, the stack of MS layers includes a layer configured to diffract light in the near infrared (N-IR) range or infrared (IR) range.

According to an aspect of some example embodiments, there is provided a see-through display configured for generating augmented reality images comprising: the optical system according to any one of claims 1-17; a frame configured to mount the optical system in relation to a user's eye; and a display configured to generate images.

Optionally, the display is a micro-display that is mounted on the frame and oriented with respect to the optical system to direct the images at an angle of 40°-50° from an optical axis of the optical system.

Optionally, the display is in the form of a visor and the micro-display is mounted on a temple of visor.

Optionally, the display includes a gaze tracking device, wherein the gaze tracking devices is configured to receive light reflected from a user's eye via the WG of the optical system.

Optionally, the display includes a camera configured to capture images of a user's eye, wherein the camera is mounted on the frame and wherein the optical system is configured to direct light reflected from the user's eye toward the camera.

Optionally, the display includes a light emitting diode (LED) configured to direct light toward a user's eye, wherein the LED is configured to emit light in a non-visible band.

Optionally, the optical system is a first optical system coupled to one eye of the user and further comprising a second optical system coupled to the other eye of the user and wherein the gaze tracking device is coupled to the second optical system.

Optionally, the second optical system includes a single MS layer coupled to a WG, wherein the single MS layer is configured to couple IR light or N-IR light reflected from a user's eye to camera of the gaze tracking device.

Optionally, the second optical system includes a first MS layer configured to couple light from the LED to the WG and from the WG to the camera and a second MS layer configured to couple light from the WG to the user's eye and from the user's eye to the WG.

According to an aspect of some example embodiments, there is provided a visor for gaze tracking comprising at least one optical system including an MS layer coupled to a waveguide (WG), wherein at least one optical system is visibly transparent, wherein the MS layer is configured to couple light in a defined non-visible spectral band, and wherein optical system is configured to direct light to the user's eye from a light source and to direct light reflected from the user's eye to a camera, wherein both the camera and the light source are displaced from a field of view (FOV) of the user.

Optionally, the MS layer is configured to diffract light in the N-IR band.

Optionally, the light source is a N-IR LED.

Optionally, the camera and the light source are mounted on a frame of the visor.

Optionally, at least one of the camera and the light source are mounted on a temple of the visor.

Optionally, the camera is integrated with a processing unit configured to track gaze based on images captured.

Optionally, the visor is configured to project augmented images.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings (including images). With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5 is a simplified schematic illustration of an example MS stack in accordance with some example embodiments;

FIGS. 6A and 6B are simplified schematic illustrations showing diffraction with a binary grating and coupling with a MS in accordance with some example embodiments;

Figure 12A:
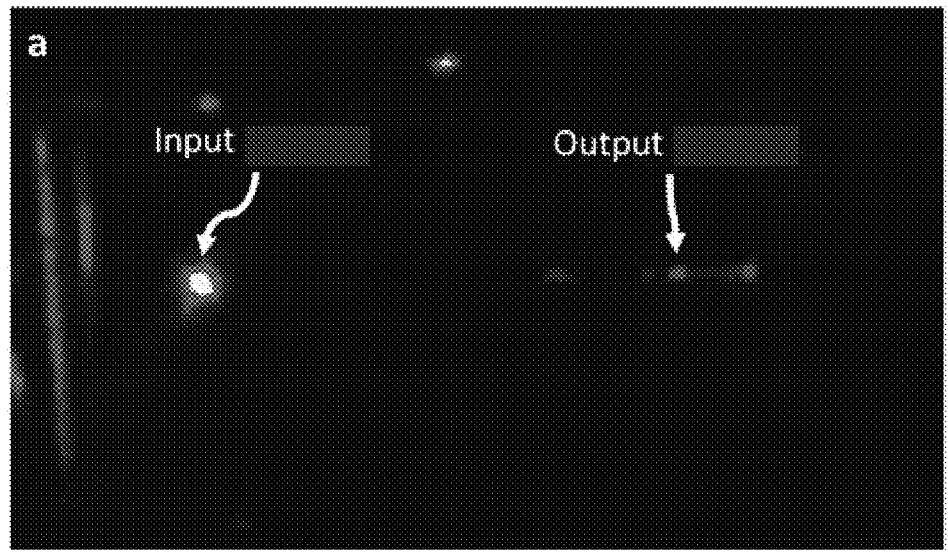
Figure 12B:
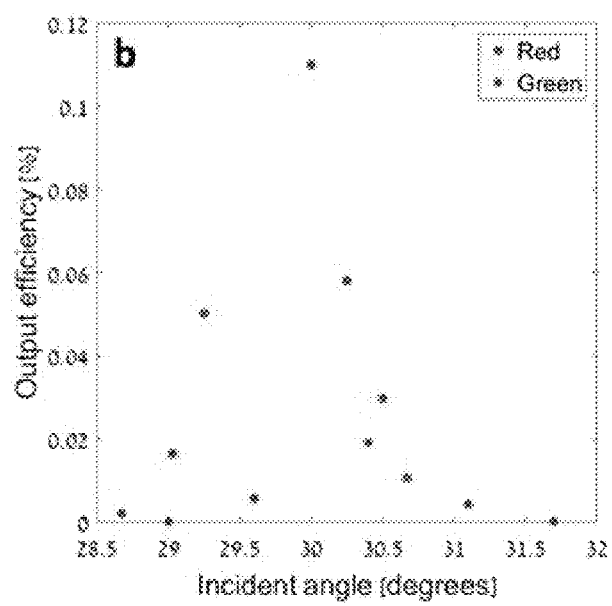
Figure 13A:
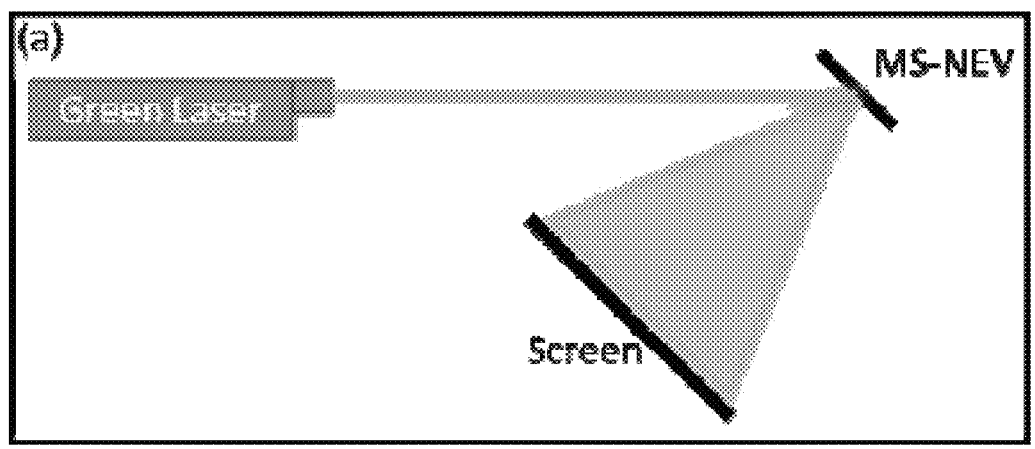
Figure 13B:
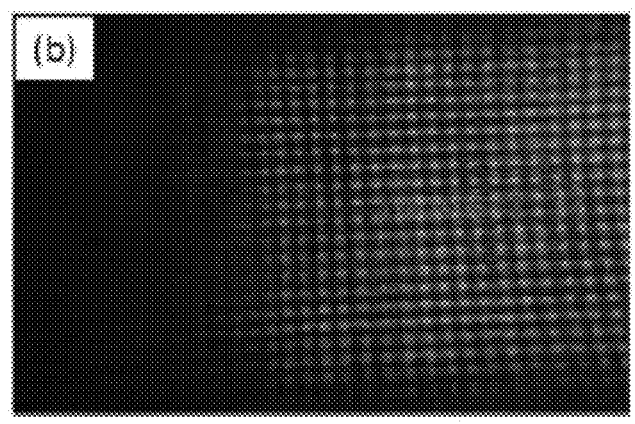
Figure 13C:
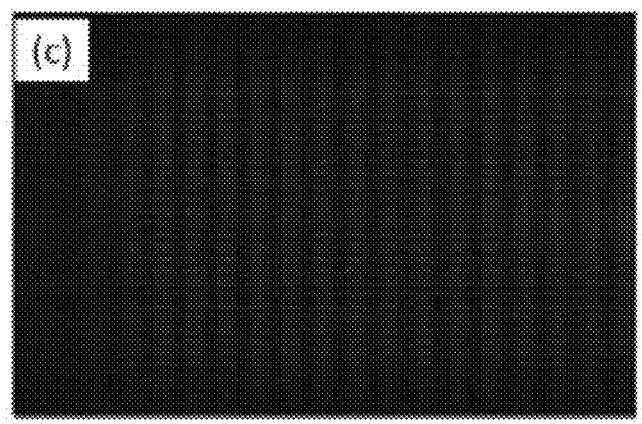

FIGS. 12A and 12B are an example image of the 633 nm laser beam, at the input (left spot) and output (right spot) of the WG and an example graph of the efficiency of the optical system as a function of incident angle for input wavelengths of 633 nm (red) and 532 nm (green) respectively, both in accordance with some example embodiments; and FIGS. 13A, 13B and 13C are a schematic drawing of an MS illuminated with a 532 nm laser source at 45°, MS, an image obtained on an optical bench setup and a simulated image obtained using beam propagation simulation respectively, all in accordance with some example embodiments.

DESCRIPTION OF SPECIFIC EMBODIMENTS OF THE INVENTION

The present invention, in some embodiments thereof, relates to a see-through display and, more particularly, but not exclusively, to a near-eye visor. In preferred embodiments, the near-eye visor serves as a display of an augmented reality system.

According to some example embodiments, the see-through display includes at least one stack of MS layers or at least one MS layer coupled to a WG. In some example embodiments, each layer in the at least one MS stack is configured provide a resonant response to an optical field and to couple light from a micro-display into the WG. In some embodiments, each layer in the at least one stack of MS layers is configured to direct light from a wave guide toward a user's eye. In some example embodiments, the see-through display includes both an input MS stack and an output MS stack. The WG may be configured to direct coupled light between a pair of stacks of MS layer or between a stack of MS layers and a grating, typically by total internal reflection (TIR).

According to some example embodiments, the MS stack comprises separate layers for interacting with red, green and blue light components. Each layer optionally and preferably comprises dielectric or plasmonic MSs, that are typically spaced apart by nanometric dielectric spacers. Each layer may be composed of a different material and designed to manipulate a specific band in the visible spectrum (e.g., red, green or blue). Optionally, the specific bands are not over-lapping bands or substantially not overlapping bands. Full color imaging may be provided based on RGB. Alternatively, other bands in the visible spectrum may be defined to provide full color imaging or only two discrete bands may be selected to provide color images.

Optionally, the nanometric dielectric spacers are silicon dioxide with thickness of 100-300 nm or 200 nm. The total optical response can therefore be engineered to operate in a broadband spectrum, corresponding to the spectral response of the single MS building block, the different layer design, and the number of stacked layers. The single surface's optical response is independent of the other layers, and can be designed separately. Based on the multi-layer design, the entire MS stack may be chromatically corrected while still maintaining an ultra-thin profile (~500 nm).

According to some example embodiments, the MS stack additionally includes a layer for manipulating non-visible light, e.g. includes four layers, e.g. red, green, blue and N-IR layer. The N-IR may provide for coupling N-IR light to a user's eye and coupling the N-IR reflected from the user's eye to a gaze tracking sensor. Optionally, the N-IR layer or other non-visible layer may be a standalone device coupled to the same WG or alternatively coupled to a dedicated WG.

According to some example embodiments, the MS stack includes layers of arrays of densely packed disc shaped metallic nano-structures. The spacing between particles may be sub-wavelength to avoid unwanted inter-particle diffraction effects, and the particles' size may also be sub-wavelength to avoid physical effects that deteriorate the desired resonant behavior of the MS.

When the MS stack is illuminated, localized surface plasmons are typically excited on the surface of the nano-structures, absorbing and scattering the incoming light, manifested as dips in the transmission spectra. The resonance wavelength for these nano-structures may be roughly linearly dependent on the nano-structure size. The linearity may provide for easily tuning the MS stack throughout the visible band. Optionally, the MSs spectral resonances may be tuned to the micro-display spectrum. As a consequence, non-resonant light may simply pass the see-through display unaffected, which enables see-through capability without the need of further complex optical design.

According to some example embodiments, the MS stack is designed to be a directional coupler so that more energy may be coupled to the WG. In some example embodiments, the directional coupler is composed of nano-structures that are other than the known disc shaped building block and may optionally be distributed in the layer by a defined pattern that may selectively eliminate certain diffraction order. In some example embodiments, the nano-structures may be spatially arranged in a Yagi-Uda antenna configuration to improve efficiency.

According to some example embodiments, the see-through display is in the form of a visor, helmet with visor or eyeglasses. In some example embodiments, a thickness of the visor lens or light shaping element is 20 nm-2 µm. In some example embodiments, a display or image generator, e.g. a micro-display is mounted on a frame of the visor, nose bridge or one or more of the visor arms, e.g. arms on which the visor is supported on the user's ear and is angled toward the transparent optical element of the visor. In some example embodiments, a light emitting diode (LED) configured to emit light toward the user eye (s) is mounted on the visor as well as a camera configured to capture images of the user's eye for gaze tracking. Optionally, the visor may be self powered, e.g. battery operated. In other example embodiments, the visor may be tethered to an external power source for powering the micro-display and optionally, the LED and camera. According to some example embodiments, the visor lens is visibly transparent so that an augmented reality may be achieved. As used herein visibly transparent means transmissive, with transmission coefficient of at least 80% to visible light Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
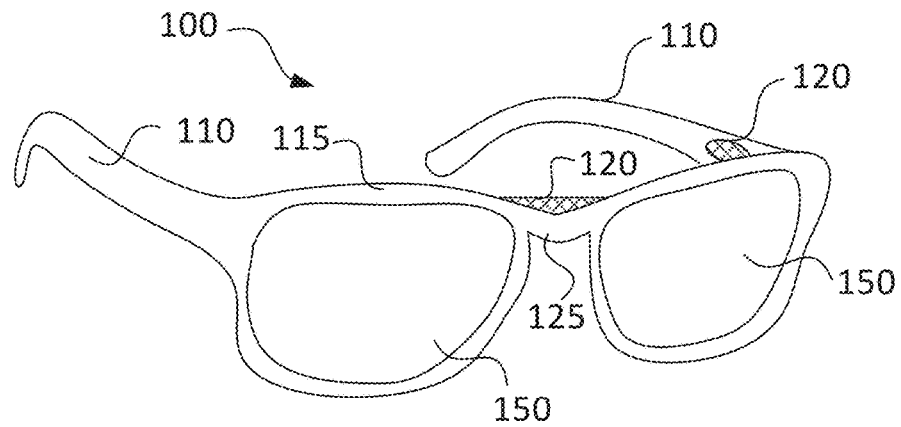
FIG. 1 is a simplified schematic illustration of an example near-eye visor in accordance with some example embodiments.

Referring now to the drawings FIG. 1 shows a simplified schematic drawing of an example near-eye visor in accordance with some example embodiments. In some example embodiments, a see-through display is in the form of eyeglasses or a visor 100 including a pair of transparent optical elements 150 through which a user may view a surrounding environment and a frame 115 configured to position transparent optical elements 150 near a user's eye. According to some example embodiments, one or both of transparent optical elements 150 includes at least one MS stack and WG to direct light between an optical device 120 of visor 100 and a user's eye. Optionally, each transparent optical element 150 includes only one WG through which a broadband spectrum may be directed.

Optical device 120 may be a micro-display configured to generate a virtual image, a LED configured to illuminate at a defined spectrum, or a camera configured to capture images of light reflected from a user's eye. Optionally, more than one optical device 120 configured to direct light between transparent optical elements 150 and a user's eye is mounted on visor 100. Optical device 120 may be mounted on arms or temples 110, on nose bridge 125 or in other parts of frame 115 of visor 100. In some example embodiments, optical device 120 may also be mounted on a helmet, head gear, or body gear that may be positioned in association with visor 100.

According to some example embodiments, visor 100 is configured to provide an augmented reality image based on optical device 120 generating an image that is directed toward a user's eye with transparent optical element 150. In some example embodiments, visor 100 is additionally or alternatively configured for eye gaze tracking based on directing light reflected off of a user eye to an optical device 120 (a camera) via transparent optical element 150.

Although visor 100 is depicted in FIG. 1 as including pair of transparent optical elements 150, in other example embodiments see-through display may be in the form of a visor with a single transparent optical element 150 that spans both eyes.

Figure 2:
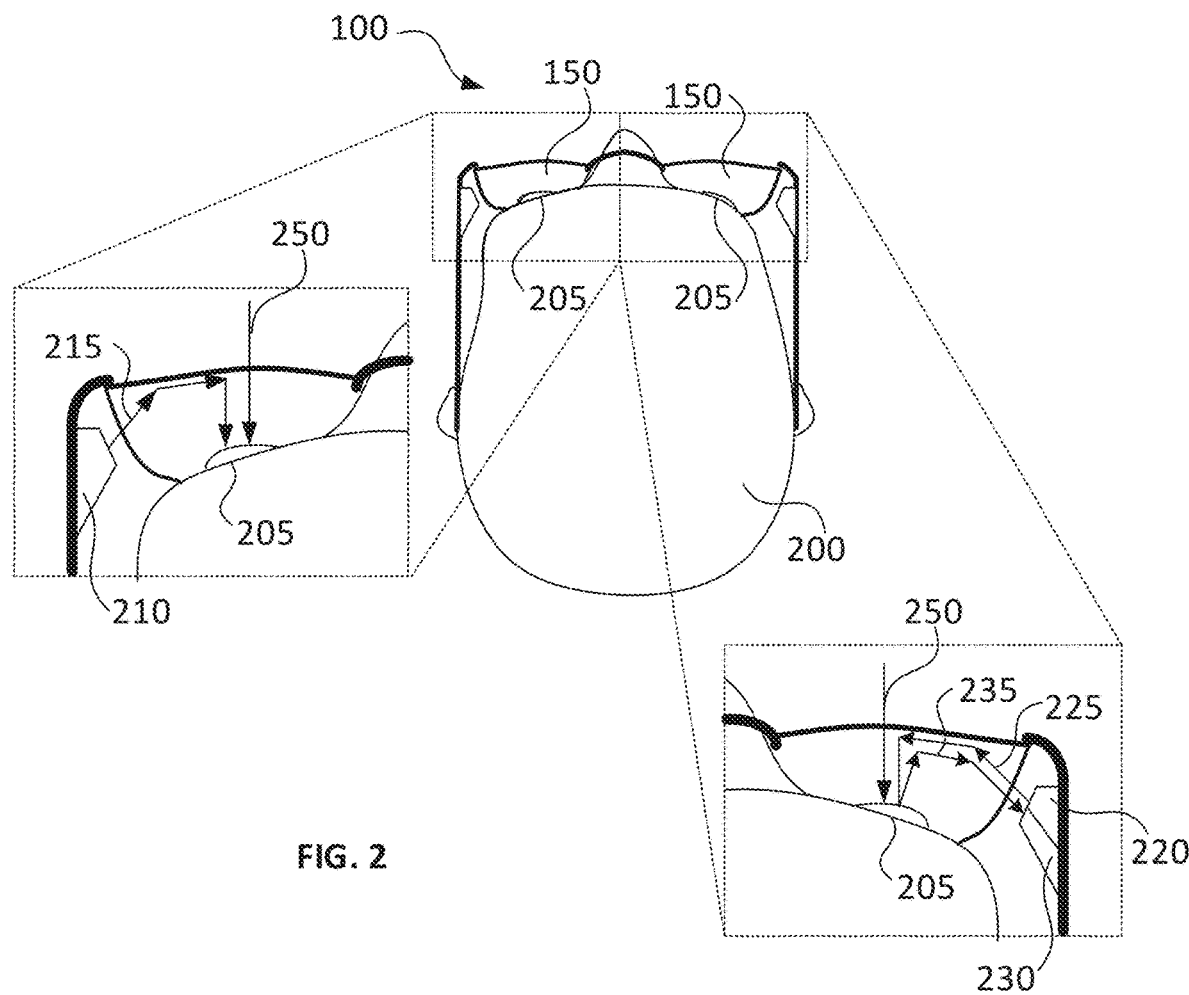
FIG. 2 is a simplified schematic illustration showing a top view of a near-eye visor worn by a user and example directions of light transmission therethrough in accordance with some example embodiments.

FIG. 2 shows a simplified schematic top view of a near-eye visor worn by a user and example directions of light transmission therethrough in accordance with some example embodiments. According to some example embodiments, visor 100 provides an augmented reality experience based on a micro display 210 generating an image and transparent optical element 150 directing the generated image toward a user's eye 205.

Optionally, micro-display is mounted on a frame or temples of visor 100 and is angled with respect to temples at an angle of 40°-50°, e.g. 45° to direct the image toward transparent optical element 150. According to some example embodiments, micro-display 210, as well as an MS stack and WG integrated on transparent optical element 150 are configured to controllably directed images generated with micro-display 210 toward user's eye 205 without obstructing the user's view of the surrounding environment, e.g. light 250 may penetrate through transparent optical element 150 while generated images are directed toward eye 205.

According to some example embodiments, visor 100 is also configured or alternatively configured to track eye gaze of user's eye 205. Eye gaze tracking may be based on a light source 220 directing light 225 toward user's eye 205 via transparent optical element 150 and capturing light 235 reflected from eye 205 and directed via transparent optical element 150 to a camera 230. Both light source 220 and camera 230 may be mounted on visor 100. Optionally, light source 220 may be in the non-visible range, e.g. N-IR so that light 225 does not obstruct visibility through transparent optical element 150. According to some example embodiments, an MS layer and WG integrated on transparent optical element 150 is configured to controllably direct light to and from eye 205 for eye gaze tracking without obstructing the user's view of the surrounding environment, e.g. light 250 may penetrate through transparent optical element 150 while tracking eye gaze. Optionally, both the visible spectrum and the non-visible spectrum are directed to and from a user's eye with a same WG and optionally a same MS stack.

In some example embodiments, when visor 100 provides both augmented reality images and eye gaze tracking, one transparent optical element 150 is configured for projecting the augmented reality images while the other transparent optical element 150 is configured to track eye gaze. In other example embodiments, projecting the augmented reality images and tracking eye gaze is performed on a same transparent optical element 150, e.g. on both transparent optical elements 150.

Figure 3A:
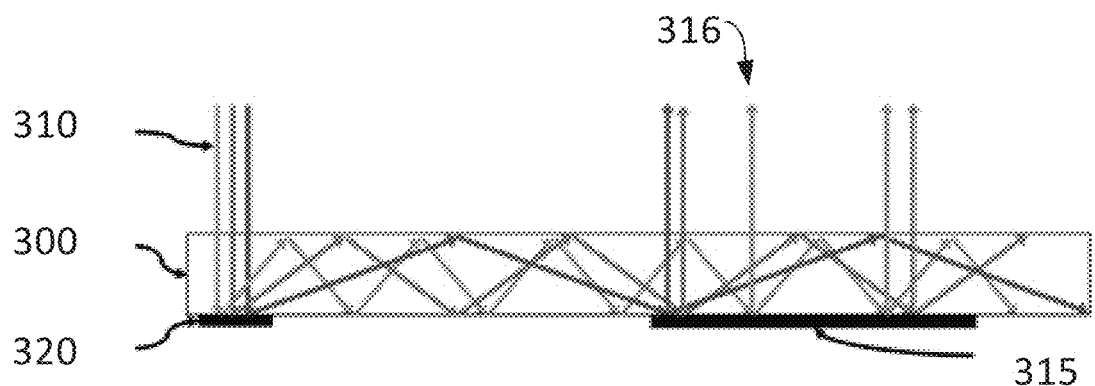
FIGS. 3A and 3B are a simplified schematic illustration of WG—grating imaging system illuminated with RGB illumination and a graph of the momentum space under RGB illumination for that system respectively.
Figure 3B:
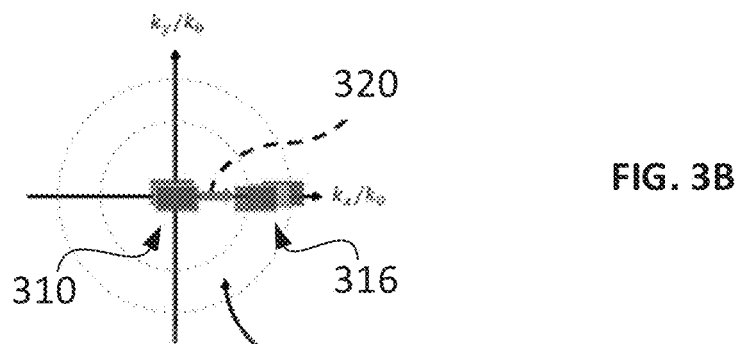

FIGS. 3A and 3B show a simplified schematic drawing of a WG—grating imaging system illuminated with RGB illumination and a graph of the momentum space under RGB illumination for that system respectively. In this system, light 310 including RGB components illuminate a first coupling in grating 320 (at the bottom left of WG 300). Coupling-in grating 320 couples light 310, e.g. from a micro-display, into WG 300, where it is guided by total internal reflection (TIR) towards a coupling-out grating 315. The coupling mechanism follows a simple momentum conservation condition, calculated using the grating equation:

$$m\lambda = an(\sin\theta_{in} \pm \sin\theta_{diff}) \quad \text{Equation (1)}$$

where, m is the diffraction order, $\lambda$ is the light's wavelength in vacuum, a is the grating period, n is the refractive index of the medium the light is propagating in, and $\theta_{in}$ and $\theta_{diff}$ are the incident and diffracted angles of the light, respectively. In addition, for a given grating period and working wavelength, the angle of incidence is bound between two limits. The first limit is given by the TIR condition, which depends on the WG's index of refraction. The second limit is given by the condition that the light ray should bounce at least once in order to reach coupling-out grating 315. When the guided light 316 reaches coupling-out grating 315, it is coupled out towards the user's eye, following the same momentum conservation condition. The angle of incidence therefore, dictates the maximum field-of-view of the system, and may be calculated to be less than 40° for typical WG parameters. Since the gratings are dispersive, each wavelength will have a different angle of incidence $\theta_{in}$ and correspondingly different $\theta_{diff}$. It follows that the total FOV of the system is wavelength dependent as shown in the graph of FIG. 3B, which is undesirable for operating under broadband illumination, e.g. RGB illumination.

Figure 3C:
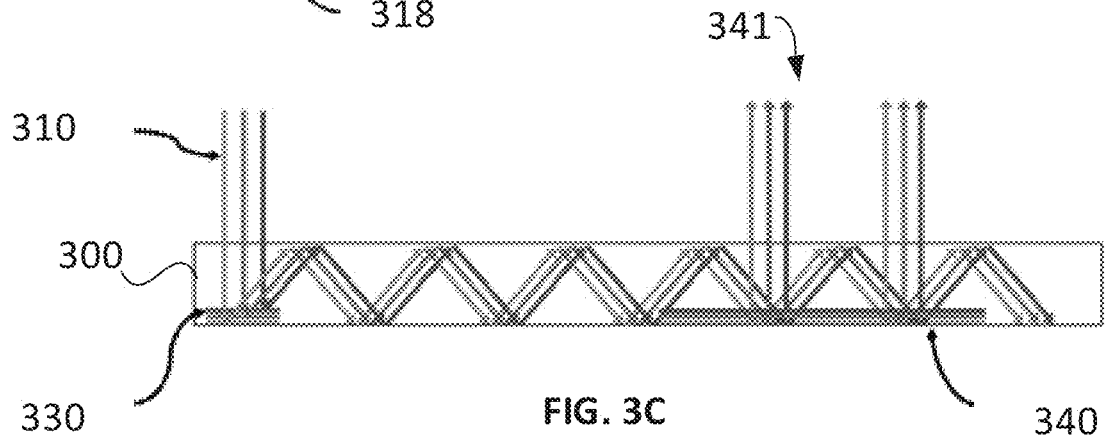
FIGS. 3C and 3D are a simplified schematic illustrations of an example WG—MS imaging system illuminated with RGB illumination and a graph of the momentum space under RGB illumination for that system respectively, both in accordance with some example embodiments.
Figure 3D:
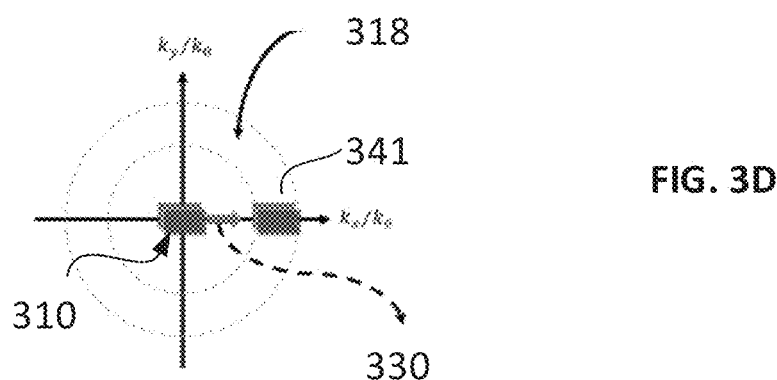

FIGS. 3C and 3D show a simplified schematic drawing of an example WG—MS imaging system illuminated with RGB illumination and a graph of the momentum space under RGB illumination for that system respectively, both in accordance with some example embodiments. The imaging system shown in FIG. 3C may be integrated in one or both of transparent optical elements 150 in shown FIG. 1 and FIG. 2 to project color images, e.g. RGB images from a micro-display toward a user's eye with WG 300. According to some example embodiments, an improved optical system 103 is obtained based on replacing coupling-in grating 320, coupling-out grating 315 or both coupling-in grating 320 and coupling-out grating 315 (FIG. 3A) with a stack of MS layers, e.g. one of first coupling device 330 or second coupling device 340 is a stack MS layers configured to couple light to and from WG 300. According to some example embodiments, the MS (first coupling device 330, second coupling device 340 or both) are composed of a stack of MS layers, each layer in the stack responsible for initiating resonance in only a specific spectral band. In some example embodiments, the MSs includes a first layer defined for red light, a second layer defined for green light and a third layer defined for blue light. Alternately, other discrete bands may be defined to provide for coupling full colored images. At the micrometer scale, each layer may be similar to a grating in that it includes a calculated period designed to obtain a FOV that is common for all layers. In this manner, the broadband image is chromatically corrected. This can be seen in the momentum space graph of FIG. 3D showing a common FOV 318 across the RGB spectrum. According to some example embodiments, WG 300 is configured to have a refractive index height than the surrounding air and is transparent for the operational range of wavelengths, e.g. visible light, N-IR and/or IR.

Figure 4A:
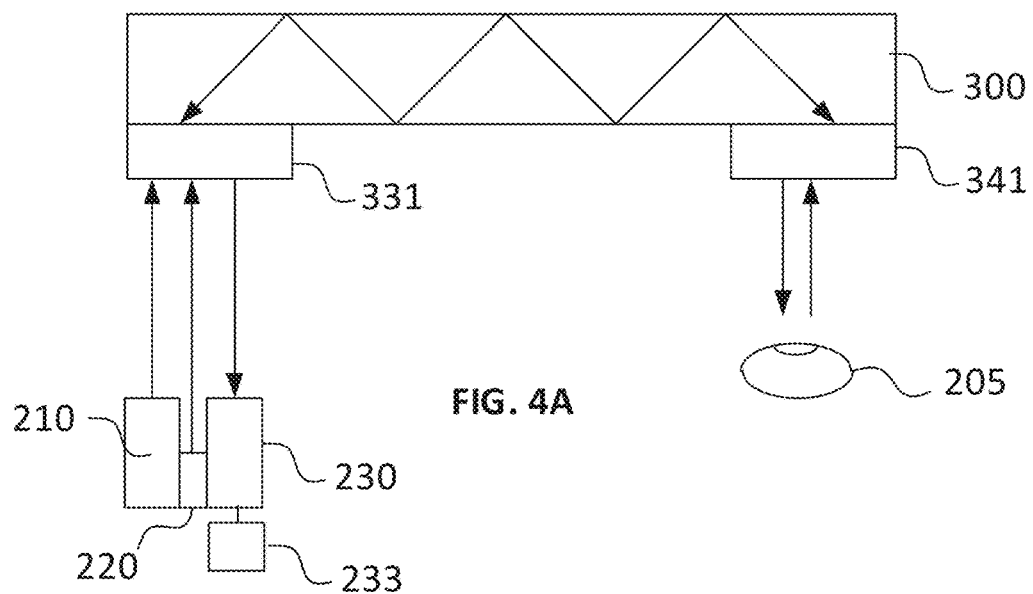
FIGS. 4A, 4B and 4C are simplified schematic illustrations of three example optical systems in accordance with some example embodiments.
Figure 4B:
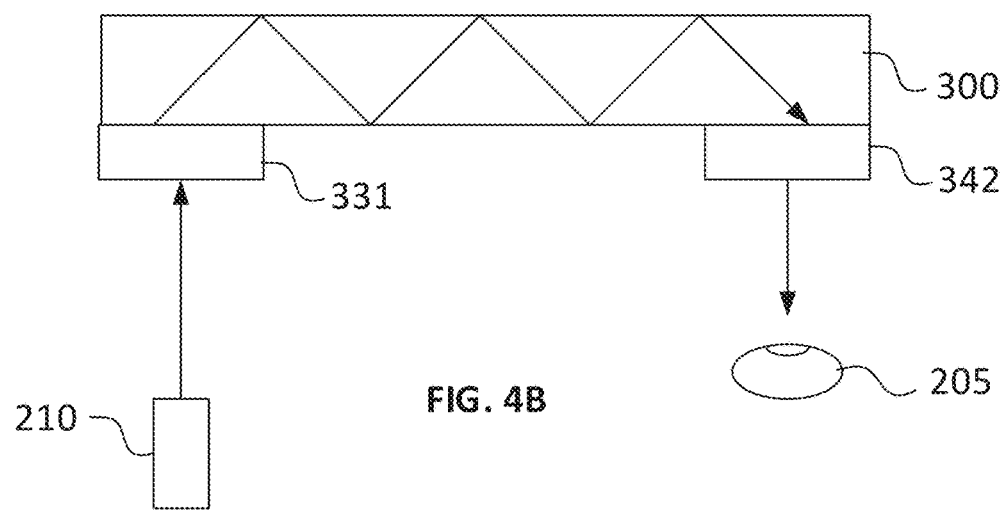
Figure 4C:
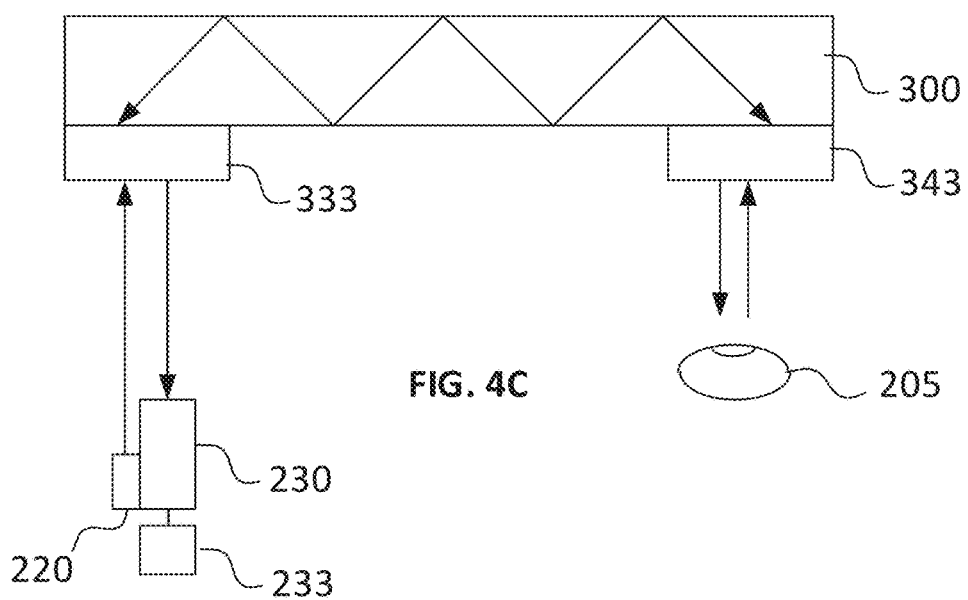

FIGS. 4A, 4B and 4C show simplified schematic drawings of three example optical system in accordance with some example embodiments. According to some example embodiments, a WG-MS imaging system 401 (FIG. 4A) is configured to both direct an image, e.g. a full colored from a display 210 to a user's eye 205 and may also be configured to direct light (optionally light outside the RGB spectrum) for capturing an image of the user's eye with a camera 230 based on light projected on eye 205 with light source 220. Optionally, camera 230 includes or is associated with a processing unit 233 configured to track gaze based on captured images. Processing unit 233 may be integrated with camera 230 or may receive input from camera 230 by tethered or wireless connection. To accommodate both full color image projection and eye gaze tracking, one or more of MS couplers 331 and 341 may optionally include at least four layers. Three of the four layers may be RGB layers as discussed in reference to FIG. 3C and a fourth layer may be configured for a non-visible spectrum, IR spectrum or an N-IR spectrum. In other example embodiments, the RGB spectrum may be substantially covered with only with two layers. Optionally, the non-visible spectrum may be applied for projecting light on eye 205 and capturing the reflected light with camera 230 for eye gaze tracking. As such, each of MS couplers 331 and 341 may be operated as an input coupler and an output coupler.

According to some example embodiments, a WG—MS imaging system 402 (FIG. 4B) is only configured for providing an augmented reality image and not for eye gaze tracking. For this purpose, one or more of MS couplers 332 and 342 may include a stack of at least two MS layers and preferably three layers to provide RGB imaging. Couplers 332 may couple image from display 210 to WG 300 and coupler 342 may couple the image from WG 300 to the user's eye 205. In this manner, coupler 332 is operated as an input coupler and grating 342 is an output coupler.

In some example embodiments, a WG—MS imaging system 403 (FIG. 4C) is only configured for eye gaze tracking. For this purpose, one or more of MS couplers 333 and 343 may include a single MS layer configured in the IR or N-IR spectrum. Optionally, couplers 333 may couple light from light source 220 and to camera 230 with WG 300 while coupler 343 may couple light to and from eye 205 to WG 300. As such each of couplers 333 and 343 are operated as both input and output gratings.

FIG. 5 shows a simplified schematic drawing of an example MS stack in accordance with some example embodiments. FIG. 5 shows three layers, but MS stack 370 may include any number of layers, preferably at least two layers. The layers, e.g. layers 361, 362 and 363 of MS stack 370 are preferably stacked along an optical axis 14. Each of layers 361, 362 and 363 may include an array nano-structures formed from a different material and/or may be sized and spaced to provide a desired response. For example, layer 361 may include disc shaped nano-structures 371 formed from gold (Au) with diameter $D_{AU}$ and spaced apart with spacing $I_{AU}$, layer 362 may include disc shaped nano-structures 372 formed from silver (Ag) with diameter $D_{AG}$ and spaced part with spacing $I_{AG}$ and layer 361 may include disc shaped nano-structures 373 formed from aluminum (AL) with diameter $D_{AL}$ and spaced apart with spacing $I_{AL}$. Optionally, spacing between nano-structures is not uniform along the layer. Typically, the nano-structures of each layer are formed on, or embedded in, a respective substrate that is transmissive to an optical field for which MS stack 370 is designed. For example, when MS stack 370 is designed for visible light (e.g., wavelength from about 400 nm to about 725 nm), substrate 370 is configured to be transmissive (e.g., with transmission coefficient of at least 80%) to visible light. Representative examples of materials suitable for use as substrate 18 include, without limitation, at least one of: glass, Indium-Tin-Oxide (ITO), silica (SiO2), and the like.

In some embodiments of the present invention the size of the nano-structures in each layer, and the spacing between the nano-structures in each layer is selected to provide a resonant response to an optical field at a different wavelength. As used herein, "resonance response" refers to a situation at which the interaction amplitude between the nano-structures and the optical field exhibits a maximum as a function of the frequency or wavelength of the optical field. In various exemplary embodiments of the invention the resonant response is a plasmonic excitation.

While a specific layer provides a resonant response to an optical field at a specific wavelength, the interaction amplitude of optical field components of wavelengths that are close to the specific wavelength is also enhanced. The resonance response of a layer is therefore characterized by a range of wavelengths for which the interaction amplitude is enhanced relative to optical field components of wavelengths that are outside this range. The specific wavelength at which the interaction amplitude exhibits a maximum is referred to as the central wavelength of the layer.

In some example embodiments, one or more of the layers of MS stack 370 includes dielectric nano-structures, e.g. nano-structures made of a dielectric material with index of refraction of at least 1.8, optionally devoid of metallic nano-structures.

According to some example embodiments, nano-structures 371, 372 and 373 are a densely packed. The spacing between particles may be sub-wavelength to avoid unwanted inter-particle diffraction effects, and the particles' size may also be sub-wavelength to avoid physical effects that deteriorate the desired resonant behavior of the MS. The single surface's optical response may be independent of the other layers, and may be designed separately.

FIGS. 6A and 6B are simplified schematic drawings showing diffraction with a conventional binary grating and a response with a MS in accordance with some example embodiments. In a conventional binary diffraction grating 160 typically includes interleaved opaque and transparent zones designed to diffract a certain frequency according to the grating equation:

$$m\lambda T = n_2 \sin \theta_{diff} - n_1 \sin \theta_{in} \quad \text{Equation (2)}$$

where $n_1$, $n_2$ are the refraction indices at the input and T is the grating frequency in lines per micrometer. When grating 160 is illuminated at a certain angle, each wavelength (light rays 163) will propagate at a different diffraction angle because of momentum considerations and diffraction angle may be tuned via the grating frequency.

According to some example embodiments, the opaque zones of the binary grating is replaced with a MS so that only a wavelength (light rays 420) at the resonance frequency may be modulated and directed to a user's eye, while the remainder of the spectrum (light rays 415), e.g. from white spectrum (light rays 410) will pass MS 360 unaffected. In some example embodiments, a plurality of MS layers are stacked and each layer in the stack directs a specific color to the same angle, by changing the nano-structures period of the individual layers in a calculated manner.

Figure 7A:
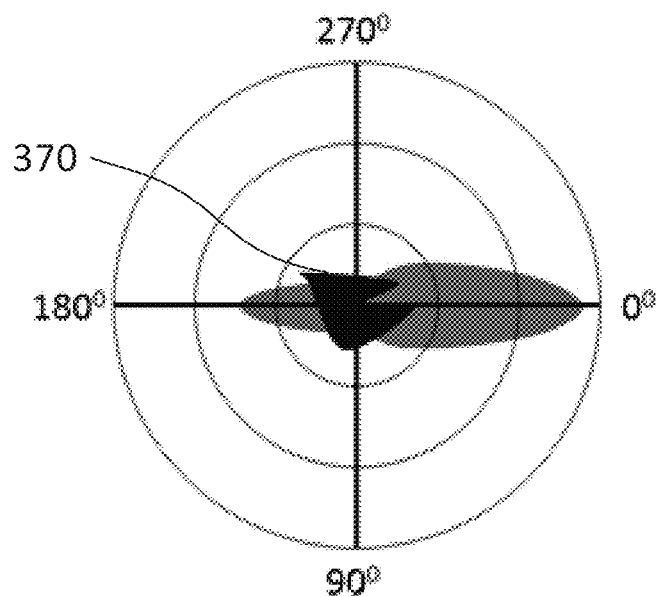
FIGS. 7A and 7B are a simplified directional radiation pattern of an example directional nano-structures and a simplified illustration of an example array of nano-structures on an MS layer respectively, both in accordance with some example embodiments.
Figure 7B:
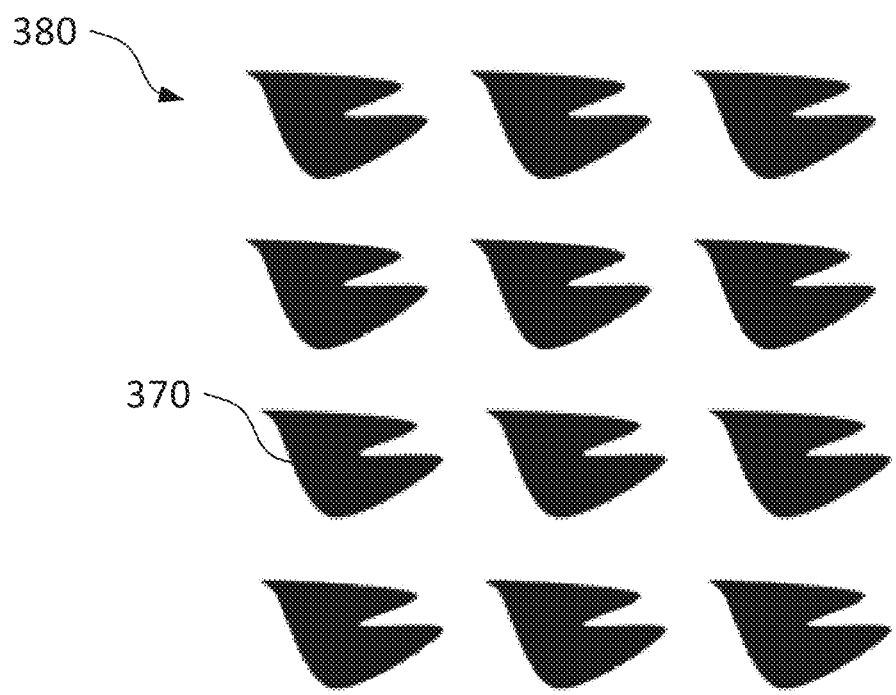

FIGS. 7A and 7B show a simplified directional radiation pattern of an example directional nano-structure and a simplified drawing of an example array of nano-structures on an MS layer respectively, both in accordance with some example embodiments. One challenge posed by simple building blocks such as disc shaped nano-structures, is that the scattering cross section may resemble that of a simple dipolar antenna. This may lead to a decreased efficiency of WG in-coupling and out-coupling since part of the signal may be scattered to unwanted directions. In some example embodiments, directional couplers are used in place of the array of disc shaped nano-structures in a binary pattern. In some example embodiments, a direction coupler includes nano-structures with a more complex shape, e.g. nano-structures 370 having a non-symmetrical shape. A corresponding directional radiation pattern of nano-structures 370 is shown in FIG. 7A. In some example embodiments, a direction coupler additionally or alternatively includes a more complex spatial arrangement of the nano-structures. Optionally, the nano-structures may be arranged in a Yagi-Uda antenna configuration to increase the efficiency of coupling. Optionally, shape and spatial distribution is selectively defined to spectrally engineer scattering pattern and/or to collectively eliminate certain diffraction orders.

Figure 8:
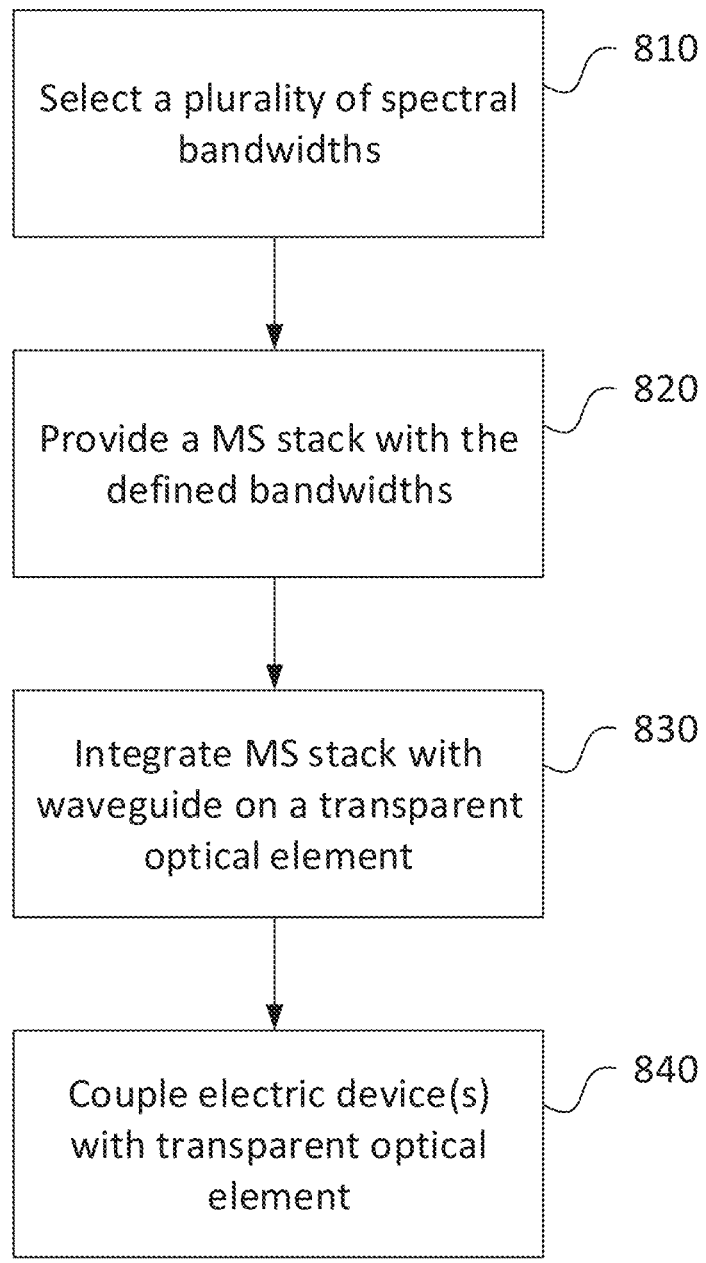
FIG. 8 is a simplified flow chart of an example method for constructing a see-through display in accordance with some example embodiments.

FIG. 8 shows a simplified flow chart of an example method for constructing a see-through display for an augmented reality imaging system in accordance with some example embodiments. According to some example embodiments, a plurality of spectral bandwidths may be selected for operating an augmented reality imaging system (block 810). The plurality of spectral bandwidths may include RGB spectrum, only a selected part of the RGB spectrum or may additionally or alternatively include bandwidths outside the RGB spectrum. Optionally, at least two spectral bandwidths are selected. The spectral bandwidths may be selected to be in the visible range for projecting virtual images toward a user's eye and may also be selected to be in the non-visual range, e.g. for imaging the user's eye for gaze tracking.

According to some example embodiments, an MS stack is provided including a layer for each of the selected bandwidths (block 820). In some example embodiments, material, size, shape, spatial distribution of the nano-structures in each layer is selectively defined to provide a desired spectral response for that layer. According to some example embodiments, the MS stack with WG is integrated on a transparent optical element of the see-through display (block 830). The MS stack may be configured as an input coupler, an output coupler or both. According to some example embodiments, one or more electrical devices are coupled to the transparent optical element (block 840). For example, a micro-display may be fixedly positioned and angled with respect to transparent optical element so that output from the micro-display is coupled to WG with a stack of MS layers or with a diffractive grating. Optionally, the electrical device is a camera that is fixedly positioned with respect to transparent optical element so that output from WG is coupled to the camera with the stack of MS layers or the diffractive grating. Electrical device may also be an LED configured to transmit light toward a user's eye.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Figure 9A:
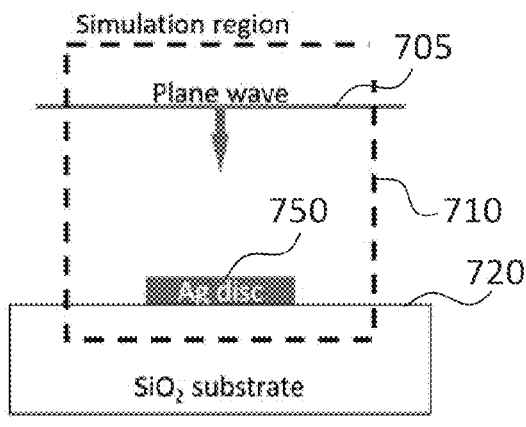
FIGS. 9A and 9B are an example single silver disc simulation scheme and transmission of the example single silver disc for several disc radii respectively, both in accordance with some example embodiments.
Figure 9C:
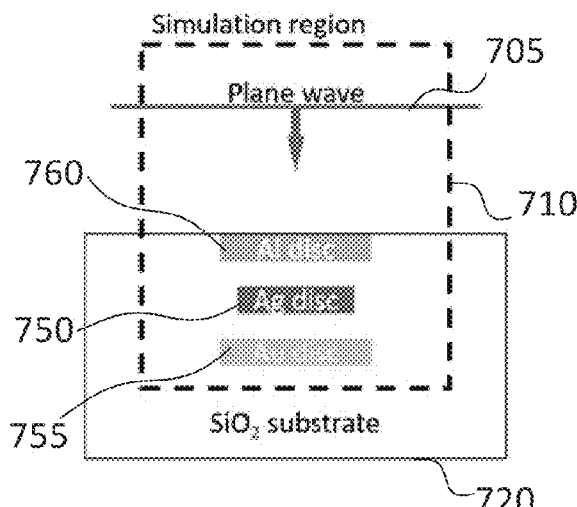
FIGS. 9C and 9D are an example three layer of metallic discs simulation scheme and transmission of Al, Ag and Au disc stack design for 450 nm, 550 nm and 650 nm respectively, both in accordance with some example embodiments.
Figure 9B:
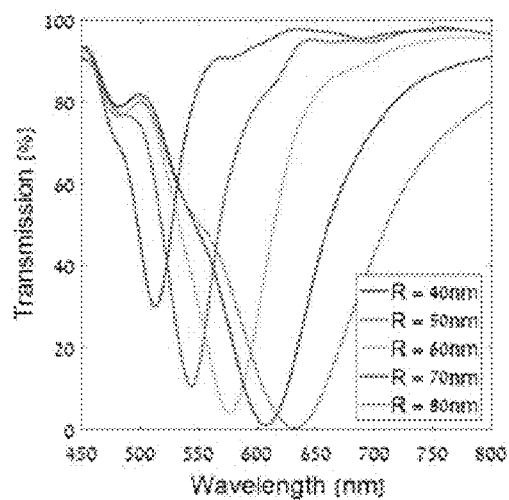
Figure 9D:
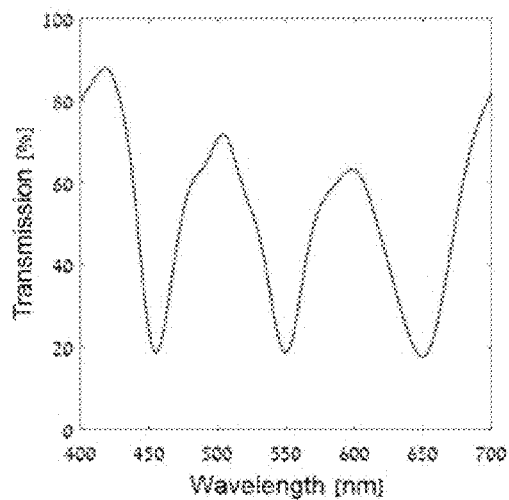

FIGS. 9A and 9B show an example single silver disc simulation scheme and transmission of the example single silver disc for several disc radii respectively, both in accordance with some example embodiments. FIGS. 9C and 9D show an example three layer of metallic discs simulation scheme and transmission of Al, Ag and Au disc stack design for 450 nm, 550 nm and 650 nm respectively, both in accordance with some example embodiments. A commercially available optical simulations software (Lumerical FDTD available by Lumerical in Canada) was applied to simulate the spectral properties of the different layers composing the MS. FIG. 9A shows an FDTD simulation scheme of a single nano size silver particle. In FIG. 9B, the transmission spectra of this particle is shown for several radii. It was found that the resonance's center wavelength was red-shifted as the particle radius is increased. In some example embodiments, such a dependence may be utilized to design a stack of three different types of nano-structures, each for a different color in the visible spectrum. FIG. 9C shows an FDTD simulation scheme of three discs made from Al, Ag and Au with radii that correspond to resonances at 450 nm, 550 nm and 650 nm respectively. The discs were spaced with a dielectric layer of 200 nm silica. In FIG. 9D, the three resonance transmission spectrum of this stack is shown. In this example, the inter-layer and inter-particle spacing were chosen to avoid strong coupling effects. Based on the selected the nano-discs' material, sizes and spacing, it is observed that minimal spectral overlap was obtained while achieving deep transmission dips.

Example 2

Figure 10A:
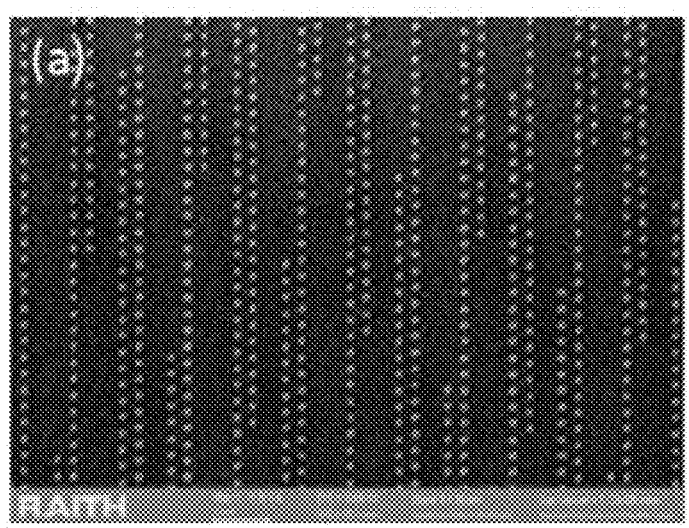
FIGS. 10A and 10B are a scanning electron microscope image of a sample gold MS and a zoomed-in section of the sample respectively, both in accordance with some example embodiments.
Figure 10B:
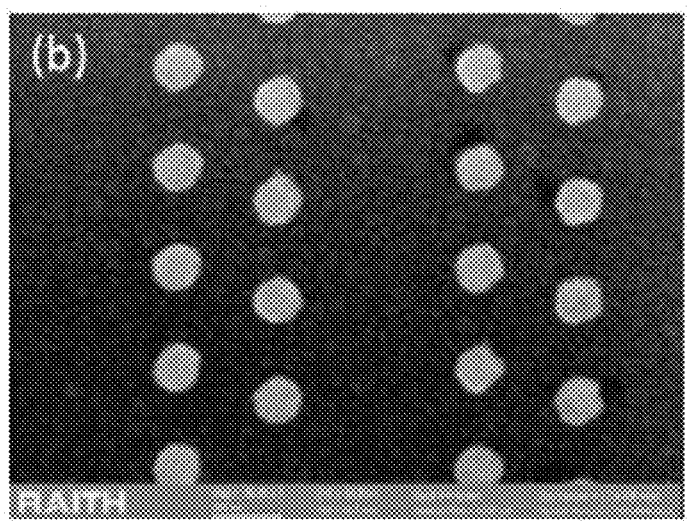

FIG. 10A shows a scanning electron microscope image of a sample gold MS. FIG. 10B shows a zoomed-in section of the sample. A periodic nature of the sample, composed of arrays of gold nanodiscs is clearly visible. It is seen that the nanodiscs are relatively uniform. The measured diameter was 140 nm±4 nm, with inter-particle spacing of 180 nm±8 nm. Improved performance may be achieved by altering particle size and inter-particle spacing. Optionally, a duty cycle of a periodic function of the sample may also be altered to widen the nanodiscs zone's width.

Example 3

Figure 11A:
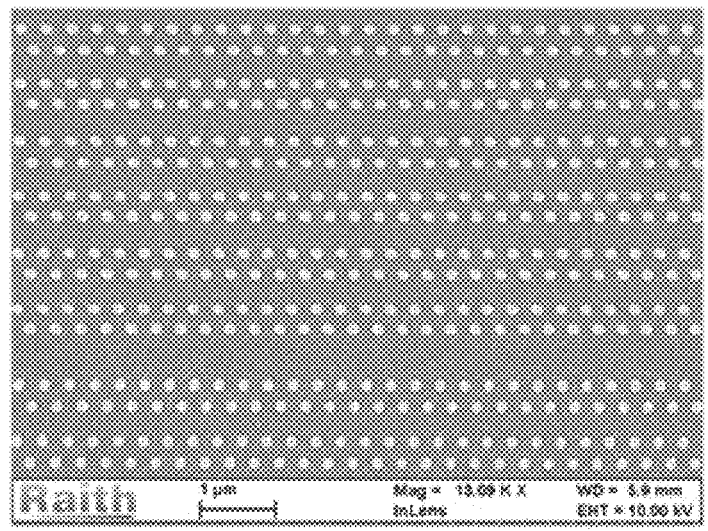
FIGS. 11A and 11B are a scanning electron microscope image of an aluminum MS and a zoomed-in section of the MS respectively, both in accordance with some example embodiments.
Figure 11B:
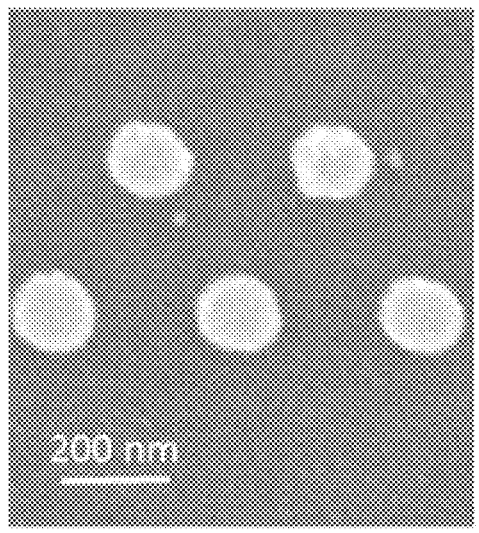

FIG. 11A shows a scanning electron microscope image of an aluminum MS. The MS is a single MS binary plasmonic MS, designed to manipulate red light. The nano-structures sizes are 130±5 nm with an inter-particle spacing of 200 nm. FIG. 11B shows a zoomed-in section of the MS. The MS was fabricated using e-beam lithography (Raith e-Line). An indium-tin-oxide covered glass was used as the substrate. After the e-beam process, 40 nm thick Aluminum film was then deposited by e-beam evaporation and subsequently lifted off.

Example 4

Performance of a fabricated device including an input MS, a WG and an output MS was analyzed while illuminating an input MS with a 633 nm laser source at 30°. FIG. 12A shows an image of the 633 nm laser beam, at the input (left spot) and output (right spot) of the WG. Distance between the input and output MS is 2.5 cm. On the right side of the image, the middle red dot is the outgoing beam after it traveled along the waveguide and exited through an MS layer. A first diffracted order of the output MS was examined. At incident angle of 30° the efficiency of the device was found to be more than 0.1%. The red dots in FIG. 12B show the efficiency of the optical system as a function of incident angle for input wavelengths of 633 nm (red) and 532 nm (green). The devices were optimized for light at a wavelength of 633 nm and incident angle of 30°. The green dots represent the efficiency of a similar device illuminated with a 532 nm laser source, which clearly represent a significant drop in coupling efficiency, as desired.

Example 5

A MS was illuminated with 532 nm laser source at 45° to analyze performance of a fabricated device including an input MS, a WG and an output MS. FIG. 13A shows a schematic drawing of an MS illuminated with a 532 nm laser source at 45°. FIG. 13B shows an image obtained on an optical bench setup. FIG. 13C shows a simulated image obtained using beam propagation simulation. The simulation was done by implementing a Fourier transfer function approach in MATLAB.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. An optical system for a see-through display, the system comprising:
    a stack of metasurface (MS) layers configured to receive light constituting an image; and
    a waveguide (WG) coupled to the stack,
    wherein each layer in the stack of MS layers is configured to provide a resonant response that enhances an interaction amplitude of an optical field at a different spectral band and to couple the resonant response with a WG, wherein the WG is configured to propagate the different spectral bands in a direction of a user's eye;
    wherein each layer in the stack of MS layers comprises nano-structures made of a different material, wherein the different material is different metal or dielectric material, and wherein the nano-structures of at least one layer of the stack of MS layers are configured to have an asymmetrical shape.

2. The system of claim 1, wherein the stack of MS layers includes a first layer configured to initiate a resonant response to red light, a second layer configured to initiate a resonant response to green light and a third layer configured to initiate a resonant response to blue light.

3. The system of claim 1, wherein the light is provided by an external source and wherein the stack of MS layers is an input coupler configured to couple light from the external source to the WG.

4. The system of claim 1, wherein the stack of MS layers is an output coupler configured to couple light in the WG to the user's eye.

5. The system of claim 1, wherein the light is provided by an external source and wherein the stack of MS layers is a first stack of MS layers configured to couple light from the external source to the WG and further comprising a second stack of MS layers configured to couple light in the WG to the user's eye, wherein the first stack of MS layers and the second stack of MS layers are configured to span a same spectral band.

6. The system of claim 1, wherein each layer in the stack of MS layers is configured as a binary diffractive element.

7. The system of claim 1, wherein the WG provides total internal reflection (TIR) therein.

8. The system of claim 1, wherein the stack of MS layers comprises a first layer having gold nano-structures sized and spaced apart to provide a resonant response to an optical field at a first wavelength, a second layer having silver nano-structures sized and spaced apart to provide a resonant response to an optical field at a second wavelength being shorter than the first wavelength, and a third layer having aluminum nano-structures sized and spaced apart to provide a resonant response to an optical field at a third wavelength being shorter than the second wavelength.

9. The system of claim 1, wherein the stack of MS layers is configured to be a directional coupler.

10. The system of claim 1, wherein the nano-structures of at least one layer of the stack of MS layers distributed in a Yagi-Uda antenna configuration.

11. The system of claim 1, wherein the stack of MS layers includes a layer configured to diffract light in the near infrared (N-IR) range or infrared (IR) range.

12. A see-through display configured for generating augmented reality images comprising:
the optical system according to claim 1;
a frame configured to mount the optical system in relation to a user's eye; and
a display configured to generate images.

13. The display of claim 12, wherein the display is a micro-display that is mounted on the frame and oriented with respect to the optical system to direct the images at an angle of 40°-50° from an optical axis of the optical system, wherein the display is in the form of a visor and the micro-display is mounted on a temple of visor.

14. The display of claim 12, comprising a gaze tracking device including a camera configured to capture images of a user's eye, wherein the camera is mounted on the frame and wherein the optical system is configured to direct light reflected from the user's eye toward the camera, wherein the camera is configured to receive light reflected from a user's eye via the WG of the optical system.

15. The display of claim 14, comprising a light emitting diode (LED) configured to direct light toward a user's eye, wherein the LED is configured to emit light in a non-visible band.

16. The display of claim 15, wherein the optical system is a first optical system coupled to one eye of the user and further comprising a second optical system coupled to the other eye of the user and wherein the gaze tracking device is coupled to the second optical system and wherein the second optical system includes a single MS layer coupled to a WG, wherein the single MS layer is configured to couple IR light or N-IR light reflected from a user's eye to camera of the gaze tracking device.

17. The display of claim 16, wherein the second optical system includes a first MS layer configured to couple light from the LED to the WG and from the WG to the camera and a second MS layer configured to couple light from the WG to the user's eye and from the user's eye to the WG.

18. A visor for gaze tracking comprising at least one optical system including a stack of MS layers coupled to a waveguide (WG), wherein the at least one optical system is visibly transparent, wherein one of the MS layers is configured to couple light in a defined non-visible spectral band, and wherein optical system is configured to direct light to the user's eye from a light source and to direct light reflected from the user's eye to a camera, wherein both the camera and the light source are displaced from a field of view (FOV) of the user, wherein the one MS layer is configured to diffract light in the N-IR band.

19. The visor of claim 18, wherein the light source is a N-IR LED.

20. The visor of claim 18, wherein the camera and the light source are mounted on a frame of the visor.

21. The visor of claim 18, wherein at least one of the camera and the light source are mounted on a temple of the visor.

22. The visor of claim 18, wherein the camera is integrated with a processing unit configured to track gaze based on images captured.

23. The visor of claim 18, further configured to project augmented images.

24. A see-through display configured for generating augmented reality images comprising:
a first optical system coupled to a first eye of a user, and comprising a stack of metasurface (MS) layers configured to receive light constituting an image, and a waveguide (WG) coupled to the stack, wherein each layer in the stack of MS layers is configured to provide a resonant response that enhances an interaction amplitude of an optical field at a different spectral band and to couple the resonant response with a WG, wherein the WG is configured to propagate the different spectral bands in a direction of the eye;
a frame configured to mount the optical system in relation to a user's eye;
a display configured to generate images;
a gaze tracking device including a camera configured to capture images of a second eye, wherein the camera is mounted on the frame;
a light emitting diode (LED) configured to direct light toward the second eye, wherein the LED is configured to emit light in a non-visible band; and
a second optical system coupled to the second eye of the user, wherein the gaze tracking device is coupled to the second optical system and the second optical system is configured to direct light reflected from the second eye toward the camera, wherein the second optical system includes a single MS layer coupled to a WG, wherein the camera is configured to receive light reflected from the second eye via the WG of the second optical system, wherein the single MS layer is configured to couple IR light or N-IR light reflected from the second eye to the camera of the gaze tracking device.

25. An optical system for a see-through display, the system comprising:
a stack of metasurface (MS) layers configured to receive light constituting an image; and
a waveguide (WG) coupled to the stack,
wherein each layer in the stack of MS layers is configured to provide a resonant response that enhances an interaction amplitude of an optical field at a different spectral band and to couple the resonant response with a WG, wherein the WG is configured to propagate the different spectral bands in a direction of a user's eye;
wherein each layer in the stack of MS layers comprises nano-structures made of a different material;
wherein the different material is different metal or dielectric material;
wherein the stack of MS layers comprises a first layer having gold nano-structures sized and spaced apart to provide a resonant response to an optical field at a first wavelength, a second layer having silver nano-structures sized and spaced apart to provide a resonant response to an optical field at a second wavelength being shorter than the first wavelength, and a third layer having aluminum nano-structures sized and spaced apart to provide a resonant response to an optical field at a third wavelength being shorter than the second wavelength.

26. An optical system for a see-through display, the system comprising:
a stack of metasurface (MS) layers configured to receive light constituting an image; and
a waveguide (WG) coupled to the stack,
wherein each layer in the stack of MS layers is configured to provide a resonant response that enhances an interaction amplitude of an optical field at a different spectral band and to couple the resonant response with a WG, wherein the WG is configured to propagate the different spectral bands in a direction of a user's eye;
wherein the stack of MS layers includes a layer configured to diffract light in the near infrared (N-IR) range or infrared (IR) range.

27. A see-through display configured for generating augmented reality images comprising:
an optical system;
a frame configured to mount the optical system in relation to a user's eye; and
a micro-display display, configured to generate images, and being mounted on the frame and oriented with respect to the optical system to direct the images at an angle of 40°-50° from an optical axis of the optical system, wherein the display is in the form of a visor and the micro-display is mounted on a temple of visor;
said optical system comprising a stack of metasurface (MS) layers configured to receive light constituting an image, and a waveguide (WG) coupled to the stack;
wherein each layer in the stack of MS layers is configured to provide a resonant response that enhances an interaction amplitude of an optical field at a different spectral band and to couple the resonant response with a WG, wherein the WG is configured to propagate the different spectral bands in a direction of a user's eye.

* * * * *